US012728152B2

(12) United States Patent
Goldberg et al.

(10) Patent No.: US 12,728,152 B2
(45) Date of Patent: Sep. 8, 2026

(54) GROWTH AND DIFFERENTIATION FACTOR 15 FOR TREATMENT OF PROLIFERATIVE VITREORETINOPATHY THERAPY

(71) Applicants: The Board of Trustees of the Leland Stanford Junior University, Stanford, CA (US); The United States Government as Represented by the Department of Veterans Affairs, Washington, DC (US)

(72) Inventors: Jeffrey Louis Goldberg, Menlo Park, CA (US); Kun-Che Chang, Redwood City, CA (US)

(73) Assignees: The Board of Trustees of the Leland Stanford Junior University, Stanford, CA (US); The United States Government as represented by the Department of Veterans Affairs, Washington, DC (US)

( * ) Notice: Subject to any disclaimer, the term of this patent is extended or adjusted under 35 U.S.C. 154(b) by 665 days.

(21) Appl. No.: 18/039,187

(22) PCT Filed: Dec. 7, 2021

(86) PCT No.: PCT/US2021/062207

§ 371 (c)(1),
(2) Date: May 26, 2023

(87) PCT Pub. No.: WO2022/125548

PCT Pub. Date: Jun. 16, 2022

(65) Prior Publication Data

US 2024/0000891 A1 Jan. 4, 2024

Related U.S. Application Data

(60) Provisional application No. 63/122,789, filed on Dec. 8, 2020.

(51) Int. Cl.

| | |
|---|---|
| ***A61K 38/00*** | (2006.01) |
| ***A61K 9/00*** | (2006.01) |
| ***A61K 38/18*** | (2006.01) |

(52) U.S. Cl.

CPC ........ *A61K 38/1841* (2013.01); *A61K 9/0019* (2013.01); *A61K 9/0048* (2013.01)

(58) Field of Classification Search

CPC . A61K 38/1841; A61K 9/0019; A61K 9/0048
See application file for complete search history.

(56) References Cited

U.S. PATENT DOCUMENTS

| | | | |
|---|---|---|---|
| 2018/0064708 | A1 | 3/2018 | Kazlauskas |
| 2019/0284257 | A1 | 9/2019 | Kumar et al. |

FOREIGN PATENT DOCUMENTS

WO WO-2021207282 A2 * 10/2021 ........... C12N 5/0621

OTHER PUBLICATIONS

Iwata_et_al_2021 (Year: 2021).*
Wang_et_al_Med_Sci_Monit_March_28_2020 (Year: 2020).*
Wischhusen_et_al_Front_Immunol_published_May_19_2020 (Year: 2020).*
Forfar et al "Single Amino Acid Changes Impact the Ability of *Drosophila melanogaster* Cecropins to Inhibit Growth of Providencia Pathogensâ" (ACS Omega 2025 Vol 10 pp. 5403-5414) (Year: 2025).*
Sengupta_et_al_Nucleic_Acids_Res_Nov. 2, 2018_vol. 46_No. 19_pp. 9932-9950 (Year: 2018).*
Verma_et_al_2020_Tissue_Culture (Year: 2020).*
Ilhan et al. (2016) "The Expression of GDF-15 in the Human Vitreous in the Presence of Retinal Pathologies with an Inflammatory Component". Ocul Immunol Inflamm, vol. 24(2), p. 178-183.
Ishikawa et al. (2015) "Resveratrol inhibits epithelial mesenchymal transition of retinal pigment A-epithelium and development of proliferative vitreoretinopathy". Sci Rep. vol. 5: 16386.
Idrees et al. (2019) Proliferative Vitreoretinopathy: A Review. Int Ophthalmol Clin. vol. 59(1 ). 221-240.
Klaassen et al. (2017) "Identification of proteins associated with clinical and pathological features of Proliferative diabetic retinopathy in vitreous and fibrovascular membranes". PLOS One, 011e. 2017, 1-3 vol. 12(11): e0187304.

* cited by examiner

*Primary Examiner* — Catherine S Hibbert
(74) *Attorney, Agent, or Firm* — Andrew R. Guzman; Pamela J. Sherwood; Bozicevic, Field & Francis LLP

(57) ABSTRACT

An effective dose of Growth Differentiation Factor 15 (GDF15) is used for prevention or treatment of proliferative vitreoretinopathy. Specifically, the disclosure provides methods and compositions for treatment of proliferative vitreoretinopathy (PVR), which is based on preventing or reducing proliferation, cell migration, or epithelial-mesenchymal transition (EMT) of epithelial cells involved in PVR.

16 Claims, 2 Drawing Sheets

Specification includes a Sequence Listing.

Embryonic stem cell (ESC) differentiated neural progenitor cells (NPCs)

GROWTH AND DIFFERENTIATION FACTOR 15 FOR TREATMENT OF PROLIFERATIVE VITREORETINOPATHY THERAPY

CROSS-REFERENCE TO RELATED APPLICATIONS

This application claims the benefit of U.S. provisional Patent Application Ser. No. 63/122,789, filed on Dec. 8, 2020, the contents of which are herein incorporated by reference in their entirety.

INCORPORATION BY REFERENCE OF SEQUENCE LISTING PROVIDED AS A TEXT FILE

A Sequence Listing is provided herewith in a text file, (S20-427_STAN-1805WO_ST25.txt), created on Dec. 7, 2021, and having a size of 3000 bytes. The contents of the text file are incorporated herein by reference in its entirety.

BACKGROUND

Proliferative vitreoretinopathy (PVR) is a major complication of rhegmatogenous retinal detachment (RRD) where proliferative, contractile cellular membranes form in the vitreous and on both sides of the retina, resulting in tractional retinal detachment with fixed retinal folds. PVR may be intraretinal also, causing retinal shortening. Treatment is principally surgical and often requires multiple procedures, and many anatomically successful eyes do not recover good visual function.

The development of PVR is a complex process involving humoral and cellular factors. Crucial cells in the development of PVR are retinal pigment epithelial (RPE) cells, glial cells, fibroblasts, and macrophages. Following retinal detachment and subsequent ischemia, some RPE cells lose their polarity and undergo epithelial-mesenchymal transformation (EMT). EMT is a process whereby epithelial cells lose their typical epithelial morphology and phenotype and acquire a mesenchymal-like morphology and phenotype. Various chemokines and cytokines, most notably TGF-β, PDGF10, VEGF, IL-1, 6, 8, 10 and IFN-γ11, whose presence is permitted via breakdown of the BRB, induce cell proliferation, migration, extracellular matrix deposition and contraction. Transformed cells in membranes become fibroblast-like cells that contain actin and myosin and have the ability to contract. Activation of Muller glia leads to marked gliosis within the retina that leads to retinal stiffness and shortening. Macrophages may play a multifactorial role that involves secretion of enzymes and growth factors (e.g., platelet-derived growth factor, PDGF) and transdifferentiation into fibroblast-like cells. Fibrocytes, circulating cells derived from bone marrow stem cells that transform to fibroblasts in tissue, have also been found in PVR membranes, further evincing the robust cellular buildup in response to circulating growth factors.

There is no current pharmacologic agent to treat or prevent PVR, presenting an unmet need.

SUMMARY

Methods and compositions are provided for treatment of proliferative vitreoretinopathy (PVR). An effective dose of Growth Differentiation Factor 15 (GDF15) is administered to the individual for prevention or treatment of PVR. In some embodiments the GDF15 is human GDF15. In some embodiments, delivery is intravitreal.

In some embodiments, the methods provide for preventing or reducing proliferation, cell migration, or epithelial-mesenchymal transition (EMT) of epithelial cells involved in PVR, in an individual in need thereof. In some embodiments, the epithelial cells are human epithelial cells. In some embodiments, the human epithelial cells are retinal pigment epithelial cells (RPE). In some embodiments the composition is formulated for injection. In some embodiments, the composition is formulated for intraocular injection, subretinal injection, intravitreal injection, periocular injection, subconjunctival injection, retrobulbar injection, intracameral injection, or sub-Tenon's injection.

In some embodiments, the method for treating PVR in an individual human in need thereof, comprising administering to the individual human a therapeutically effective amount of an injectable composition, comprising or consisting essentially of: (a) GDF15; and (b) a pharmaceutically acceptable diluent, excipient, vehicle, or carrier, in a dose effective to reduce the proliferation of RPE cells. In some embodiments the injectable composition consists essentially of (a) GDF15; (b) an additional therapeutic agent; and (c) a pharmaceutically acceptable diluent, excipient, vehicle, or carrier. In some embodiments, the additional therapeutic agent is an additional agent for treating PVR.

In some embodiments, the additional therapeutic agent is selected from: daunorubicin, anti-VEGF agents, methotrexate, taxol, colchicine, kinase inhibitors such as hypericin, herbimycin, alkylphosphocholine, AG1295; retinoic acid, 5-fluorouracil, intravitreal triamcinolone acetonide, ranibizumab, bevacizumab, dasatinib, pegaptanib sodium, N-acetyl-cysteine (NAC), pioglitazone, glucosamine, genistin, geldanamycin, fausdil, resveratrol, pentoxyfilline, dipyridamole, and corticosteroids. In some embodiments, the therapeutically effective amount is effective for preventing or reducing the proliferation of retinal pigment epithelial (RPE) cells. In some embodiments, the therapeutically effective amount is effective for improving outcomes associated with PVR.

In some cases, the subject suffering from or at risk of developing PVR has undergone rhegmatogenous retinal detachment surgery. A subject that is suffering from PVR is identified by presenting with any PVR indication, including without limitation the appearance of vitreous haze and retinal pigment epithelial (RPE) cells in the vitreous humor, a wrinkling of the edges of a retinal tear or the inner retinal surface, or by the presence of retinal membranes. A subject that is at risk of developing PVR is identified by presenting with any PVR risk factor, including without limitation: age, aphakia/pseudophakia, high levels of vitreous proteins, duration of retinal detachment before corrective surgery, the size of the retinal hole or tear, intra-ocular inflammation, vitreous hemorrhage, intraocular pressure, extended retinal detachments, reinterventions, scleral surgery, and trauma or injury to the eye. Other subjects at risk for developing PVR are individuals that engage in activities with increased risk for trauma or injury to or in the proximity of the eye. The subject may be an adolescent or an adult.

In some embodiments, the therapeutically effective amount of the composition has an effect on a number of different outcomes associated with PVR, which outcomes may be monitored following treatment to determine efficacy. For instance, the therapeutically effective amount of the composition may improve visual acuity, reduce the risk of PVR reoccurrence once treatment has begun, increase the rate or likelihood of retinal reattachment following rhegmatogenous retinal detachment surgery, or improve the amelioration of any other symptoms associated with PVR.

The composition may be administered at any time deemed necessary. For instance, the composition may be administered to an individual who is at risk for PVR but PVR has not yet developed, such as an individual presenting the risk factors described above. The composition may also be administered to an individual once PVR has developed. The composition may also be administered to an individual following rhegmatogenous retinal detachment surgery.

Provided herein are data showing a GDF15 effect on Smad2 pathway inhibition in retinal pigment epithelial (RPE) cell, a major cell type in the eye involved in PVR. GDF15 pretreatment reduces TGFβ-induced Smad2 phosphorylation, and its downstream EMT marker Fibronectin expression.

DETAILED DESCRIPTION OF THE EMBODIMENTS

Figure 1:
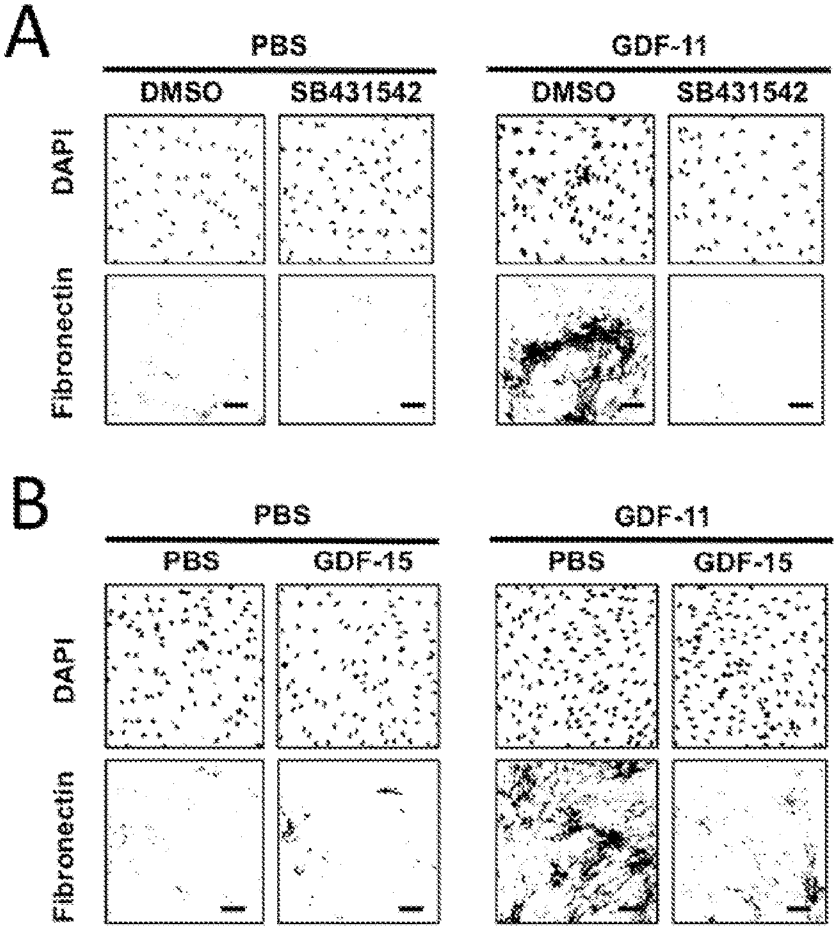
FIG. 1. Smad2 inhibition (A) or simultaneous culture with GDF-15 (B) blocks GDF-11-induced upregulation of EMT marker Fibronectin in ESC-NPCs. Scale bar=100 μm.

All structural and functional equivalents to the features and method acts of the various embodiments described throughout the disclosure that are known or later come to be known to those of ordinary skill in the art are intended to be encompassed by the features described and claimed herein. Moreover, nothing disclosed herein is intended to be dedicated to the public regardless of whether such disclosure is explicitly recited in the claims. No claim element is to be construed under the provisions of 35 USC 112, sixth paragraph, unless the element is expressly recited using the phrase "means for" or "step for".

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the term "subject" encompasses mammals and non-mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. The term does not denote a particular age or gender.

As used herein, the terms "treat," "treating" or "treatment," and other grammatical equivalents, include: alleviating, abating, or ameliorating one or more symptoms of a disease or condition. In some embodiments, treating is alleviating, abating, or ameliorating one or more symptoms of epithelial-mesenchymal transition. In some embodiments, treating is alleviating, abating, or ameliorating one or more symptoms of proliferative vitreoretinopathy.

Proliferative vitreoretinopathy (PVR) is a disease that develops as a complication of rhegmatogenous retinal detachment. When fluid from the vitreous humor enters a hole in the retina and accumulates in the subretinal space, the tractional force of the vitreous on the retina is what results in rhegmatogenous retinal detachment. During this process the retinal cell layers come in contact with vitreous cytokines, which can trigger the retinal pigmented epithelium (RPE) to proliferate and migrate. The RPE cells undergo epithelial-mesenchymal transition (EMT) and develop the ability to migrate out into the vitreous. During migration of the RPE, these cells lay down fibrotic membranes which contract and pull at the retina, and can lead to secondary retinal detachment after primary retinal detachment surgery.

Predisposing factors for postoperative PVR are preoperative PVR, aphakia, high levels of vitreous proteins, duration of retinal detachment before corrective surgery, the size of the retinal hole or tear, intra-ocular inflammation, vitreous hemorrhage, vitreous liquidity, and trauma or injury to the eye. The risk for PVR is higher in patients >70 years, with intraocular pressure lower than 14, in retinal breaks larger than "1 clock hour", extended retinal detachments, and reinterventions. Scleral surgery is a risk factor for PVR and aphakia/pseudophakia when scleral surgery is performed. In particular, some subjects that have undergone ocular surgeries, such as surgery to correct retinal detachments, are at increased risk for developing PVR.

Intraoperative risk factors for PVR development include vitreous or subretinal hemorrhage, inability to completely seal a retinal tear, intraoperative choroidal detachment, pigment release during endodrainage, excessive cryotherapy and endolaser, and vitreous loss during external subretinal fluid drainage. Postoperative risk factors for inducing PVR formation include prolonged inflammation or uveitis, intraocular hemorrhage after surgery, choroidal detachment, use of air or sulfur hexafluoride ($SF_6$) or air, multiple surgical procedures, and persistent traction on retinal breaks. The only identified modifiable risk factor associated with PVR is cigarette smoking.

PVR severity is classified based on three different classification schemes. The three main classification schemes for proliferative vitreoretinopathy (PVR) are The Retina Society Terminology Classification (1983), the Silicone Study Classification (1989), and the updated Retina Society Classification (1991).

Retina Society Terminology Committee Classification (1983)

| Grade | Clinical Signs |
|---|---|
| A (minimal) | Vitreous haze and pigment clumps |
| B (moderate) | Surface retinal wrinkling, rolled edges of the retina, retinal stiffness, and vessel tortuosity |
| C (marked) | Full-thickness fixed retinal folds in |
| (i) C-1 | (i) One quadrant |
| (ii) C-2 | (ii) Two quadrants |
| (iii) C-3 | (iii) Three quadrant |
| D (massive) | Fixed retinal folds in four quadrants that result in |
| (i) D-1 | (i) Wide funnel shape |
| (ii) D-2 | (ii) Narrow funnel shape |
| (iii) D-3 | (iii) Closed funnel without view of the optic disc |

Silicone Study Classification (1989)

| Grade | Clinical Signs |
|---|---|
| A | Vitreous haze and pigment clumps |
| B | Surface retinal wrinkling, rolled edges of the retina, retinal stiffness, and vessel tortuosity |
| P (posterior)<br>P1: One quadrant<br>(1-3 clock hours)<br>P2: Two quadrants<br>(4-6 clock hours)<br>P3: Three quadrants<br>(7-9 clock hours)<br>P4: Four quadrants<br>(10-12 clock hours)<br>(i) Type 1 (focal)<br>(ii) Type 2 (diffuse)<br>(iii) Type 3 (subretinal) | Starfolds and/or diffuse contraction in posterior retina and/or subretinal membrane in posterior retina<br>(i) Starfold<br>(ii) Confluent irregular retinal folds in posterior retina; remainder of retina drawn posterior; optic disc that may not be visible<br>(iii) "Napkin ring" around disc or "clothesline" elevation of retina |
| A (anterior)<br>A1: One quadrant<br>(1-3 clock hours)<br>A2: Two quadrants<br>(4-6 clock hours)<br>A3: Three quadrants<br>(7-9 clock hours)<br>A4: Four quadrants<br>(10-12 clock hours)<br>(i) Type 4<br>(circumferential)<br>(ii) Type 5<br>(perpendicular)<br>(iii) Type 6<br>(anterior) | Circumferential and/or perpendicular and/or anterior traction on anterior retina<br>(i) Irregular retinal folds in the anterior retina; series of radial folds more posteriorly; peripheral retina within vitreous base stretched inward<br>(ii) Smooth circumferential fold of retina at insertion of posterior hyaloids<br>(iii) Circumferential fold of retina at insertion of posterior hyaloids pulled forward; trough of peripheral retina anteriorly; ciliary processes stretched with possible hypotony; iris retracted |

Updated Retinal Society Classification (1991)

| Grade | Clinical Signs |
|---|---|
| A | Vitreous haze, pigment clumps, and pigment clusters on inferior retina |
| B | Wrinkling of inner retinal surface, retinal stiffness, vessel tortuosity, rolled and irregular edge of retinal break, and decreased mobility of vitreous |
| CP (posterior)<br>(i) Type:<br>(a) Focal<br>(b) Diffuse<br>(c) Subretinal | Full-thickness retinal folds or subretinal strands posterior to equator (1-12 clock hours of involvement)<br>(a) Starfolds posterior to vitreous base<br>(b) Confluent starfolds posterior to vitreous base; optic disc that may not be visible<br>(c) Proliferation under the retina; annular strand near disc; linear strands; moth-eaten-appearing sheets |

-continued

Updated Retinal Society Classification (1991)

| Grade | Clinical Signs |
|---|---|
| CA (anterior)<br>(i) Type:<br>(a) Circumferential<br>(b) Anterior | Full-thickness retinal folds or subretinal strands anterior to equator (1-12 clock hours involvement), anterior displacement, and condensed vitreous strands<br>(a) Retina contraction inwards at the posterior edge of the vitreous base; with central displacement of the retina; peripheral retina stretched; posterior retina in radial folds<br>(b) Anterior contraction on the retina at the vitreous base; ciliary body detachment and epiciliary membrane; iris retraction |

Given the lack of pharmacologic options for PVR, the mainstay of treatment for retinal detachments with PVR is surgical intervention. The surgical goals of retinal detachment with PVR are to reattach the retina as with all retinal detachments, however, the presence of pre- and sub-retinal membranes and intraretinal fibrosis in more severe grades of PVR often require additional maneuvers to relieve traction in order to reattach the retina and prevent re-detachment. The ideal timing of surgery for PVR is controversial. Some propose that the presence of clinical signs of activity may be an indicator to delay surgical intervention by a few weeks because the controlled trauma induced by additional surgery could stimulate additional cellular proliferation. Epiretinal proliferation in PVR takes an average of 6-12 weeks to develop completely. Delaying surgery would allow greater ease with membrane peel and ensure a more complete removal of the membranes. The decision to delay surgery must be balanced with the macula status and implications on visual recovery potential with further delay.

Despite repeated interventions, 10-40% of retinal detachments with PVR cases remain attached despite repeated surgery attempts. In one study of complicated retinal detachments mostly involving proliferative vitreoretinopathy, only 39% remained attached long term after a mean follow up period of 30 months when vitrectomy with heavy silicone oil (SiO) tamponade was used. Furthermore, even with anatomic success, patients can have poor visual outcomes. Visual acuity of 5/200 or better was achieved in 40-80% of patients after repair of retinal detachments with PVR. The poor functional results have been attributed to possible changes in the macula, such as RPE irregularities, macular pucker, cystoid macular edema, and subretinal fibrosis. These changes could also be a result of macroscopic changes secondary to formation of epiretinal, intraretinal, or subretinal membranes. Anterior PVR and multiple surgeries for repair are associated with worse visual outcomes. In patients that demonstrate anatomic and functional success three years after their last surgery, there is a high likelihood that results will be maintained long term.

By the terms "effective amount" and "therapeutically effective amount" of a formulation or formulation component is meant a sufficient amount of the formulation or component, alone or in a combination, to provide the desired effect. For example, by "an effective amount" is meant an amount of GD15, alone or in a combination, required to treat or prevent PVR in a mammal. Ultimately, the attending physician or veterinarian decides the appropriate amount and dosage regimen.

The effective dose of a therapeutic composition to be given to a particular patient will depend on a variety of factors, several of which will be different from patient to patient. Utilizing ordinary skill, the competent clinician will be able to optimize the dosage of a particular therapeutic or imaging composition in the course of routine clinical trials.

GDF 15 is a secreted ligand of the TGF superfamily of proteins. Ligands of this family bind various TGF receptors leading to recruitment and activation of SMAD family transcription factors that regulate gene expression. The encoded preproprotein is proteolytically processed to generate each subunit of the disulfide-linked homodimer. The protein is expressed in a broad range of cell types, acts as a pleiotropic cytokine and is involved in the stress response program of cells after cellular injury. Increased protein levels are associated with disease states such as tissue hypoxia, inflammation, acute injury, and oxidative stress. The sequence of human GDF15 can be accessed at Genbank, refseq NP_004855 (protein) and NM_004864 (mRNA). An exemplary amino acid sequence of human GDF-15 protein is:

(SEQ ID NO: 1)

```
MPGQELRTVNGSQMLLVLLVLSWLPHGGALSLAEASRASFPGPSELHSED

SRFRELRKRYEDLLTRLRANQSWEDSNTDLVPAPAVRILTPEVRLGSGGH

LHLRISRAALPEGLPEASRLHRALFRLSPTASRSWDVTRPLRRQLSLARP

QAPALHLRLSPPPSQSDQLLAESSSARPQLELHLRPQAARGRRRARARNG

DHCPLGPGRCCRLHTVRASLEDLGWADWVLSPREVQVTMCIGACPSQFRA

ANMHAQIKTSLHRLKPDTVPAPCCVPASYNPMVLIQKTDTGVSLQTYDDL

LAKDCHCI.
```

Similar to other members of the TGF-β superfamily, GDF15 is formed as a full-length dimer protein and is cleaved at an RXXR site with the secretion of a mature dimeric protein. The pro-GDF15 consists of 167 amino acids and contains an N-linked glycosylation site at amino acid position 70. It undergoes dimerization by a specific disulfide linkage to form the pro-GDF15 dimeric precursor. The pro-protein dimer undergoes proteolytic cleavage catalyzed by furin-like protease at the amino acid target sequence RXXR to release C-terminal dimeric mature GDF15. The mature dimer and the pro-GDF15 are then secreted into the extracellular matrix. GDF15 may exist in multiple forms within the cell: the pro-GDF15 monomer (~40 kDa), the pro-GDF15 dimer (~80 kDa), and the mature dimer (~30 kDa). In addition, the GDF15 precursor protein contains an N-terminal signal peptide.

For therapeutic methods of the disclosure, an individual may be treated with human GDF-15, or a biologically active fragment or variant thereof, including without limitation mature GDF-15 dimers. Human GDF15 is synthesized as pro-GDF15, which then dimerizes through cysteine residues to form pro-GDF15 dimer, it is then cleaved at an RXXR site, forming a 112 amino acid C-terminal dimeric protein and a pro-peptide. The carboxy-terminal domain of GDF-15 contains the characteristic seven conserved cysteine residues necessary for the formation of the cysteine knot and the single interchain disulfide bond.

The sequence of a GDF15 protein may be altered in various ways known in the art to generate targeted changes in sequence. The polypeptide will usually be substantially similar to the sequences provided herein, i.e. will differ by at least one amino acid, and may differ by at least two but not more than about ten amino acids. The sequence changes may be substitutions, insertions, or deletions. Scanning mutations that systematically introduce alanine, or other residues, may be used to determine key amino acids. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine). The polypeptide may be truncated at the C-terminus or the N-terminus by, for example, about 1, about 2, about 3, about 4, about 5, about 6, about 7, about 8, about 9, about 10, or more amino acids, provided that the truncated peptide retains substantially the same biological activity as the native protein, or native mature dimer.

Modifications of interest that do not alter primary sequence include chemical derivatization of polypeptides, e.g., acetylation, or carboxylation. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the subject invention are polypeptides that have been modified using ordinary molecular biological techniques and synthetic chemistry so as to improve their resistance to proteolytic degradation or to optimize solubility properties or to render them more suitable as a therapeutic agent. For examples, the backbone of the peptide may be cyclized to enhance stability (see Friedler et al. (2000) J. Biol. Chem. 275:23783-23789). Analogs of such polypeptides include those containing residues other than naturally occurring L-amino acids, e.g. D-amino acids or non-naturally occurring synthetic amino acids.

The subject peptides may be prepared by in vitro synthesis, using conventional methods as known in the art. Various commercial synthetic apparatuses are available, for example, automated synthesizers by Applied Biosystems, Inc., Foster City, Calif., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

The bioactivity of PVR vitreous depends on three classes of growth factors: vascular endothelial growth factor (VEGF), platelet-derived growth factor (PDGF), and non-PDGFs (growth factors outside of the PDGF family). The scheme shows the functional relationship for these growth factors and the signaling events and cellular responses triggered by indirectly activated PDGFRα. VEGF competitively inhibits PDGF-dependent activation of PDGFRα. This direct mode of activating PDGFRα antagonizes the indirect mode of activating PDGFRα, which is driven by non-PDGFs. Indirectly activated PDGFRα promotes TP53 reduction, a key event in driving PVR, because TP53 suppression promotes the viability of cells displaced into the vitreous and also mediates the contraction of PVR membranes formed from these cells; both outcomes are likely to contribute to retinal detachment.

"Anti-VEGF agent" as used herein is any substance that decreases signaling by the VEGF-VEGFR pathway. Anti-VEGF agents can be, to name just a few examples, small molecules, peptides, polypeptides, proteins, including more specifically antibodies, including anti-VEGF antibodies, anti-VEGFR antibodies, intrabodies, maxibodies, minibodies, diabodies, Fc fusion proteins such as peptibodies, receptibodies, soluble VEGF receptor proteins and fragments, and a variety of others. Many Anti-VEGF agents work by binding to VEGF or to a VEGF receptor. Others work more indirectly by binding to factors that bind to VEGF or to a VEGF receptor or to other components of the VEGF signaling pathway. Still other Anti-VEGF agents act by altering regulatory posttranslational modifications that modulate VEGF pathway signaling. Anti-VEGF agents in accordance with the invention also may act through more indirect mechanisms. Whatever the mechanism involved, as used herein, an Anti-VEGF agent decreases the effective activity of the VEGF signaling pathway in a given circumstance over what it would be in the same circumstance in the absence of the inhibitor.

A great many anti-VEGF agents have been described in the literature. In addition to those described in further detail below, Anti-VEGF agents are described in the following patent documents: US 2003/0105091, US2006/0241115, U.S. Pat. Nos. 5,521,184, 5,770,599, 6,235,764, 6,258,812, 6,515,004, 6,630,500, 6,713,485, WO2005/070891, WO 01/32651, WO 02/68406, WO 02/66470, WO 02/55501, WO 04/05279, WO 04/07481, WO 04/07458, WO 04/09784, WO 02/59110, WO 99/450029, WO 00/59509, WO 99/61422, WO 00/12089, WO 00/02871, and WO 01/37820, particularly in parts pertinent to Anti-VEGF agents.

The following are among specific anti-VEGF agents: ABT-869 (Abbott) including formulations for oral administration and closely related Anti-VEGF agents; AEE-788 (Novartis) (also called AE-788 and NVP-AEE-788, among others) including formulations for oral administration and closely related Anti-VEGF agents; AG-13736 (Pfizer) (also called AG-013736) including formulations for oral administration and closely related Anti-VEGF agents; AG-028262 (Pfizer) and closely related Anti-VEGF agents; Angiostatin (EntreMed) (also called CAS Registry Number 86090-08-6, K1-4, and rhuAngiostatin, among others) and closely related inhibitors as described in, among others, U.S. Pat. Nos. 5,792,825 and 6,025,688, particularly in parts pertaining to Angiostatin and closely related Anti-VEGF agents, their structures and properties, and methods for making and using them; Avastin™ (Genentech) (also called bevacizumab, R-435, rhuMAB-VEGF, and CAS Registry Number 216974-75-3, among others) and closely related Anti-VEGF agents; AVE-8062 (Ajinomoto Co. and Sanofi-aventis) (also called AC-7700 and combretastatin A4 analog, among others), and closely related Anti-VEGF agents; AZD-2171 (AstraZeneca) and closely related Anti-VEGF agents; Nexavar® (Bayer AG and Onyx) (also called CAS Registry Number 284461-73-0, BAY-43-9006, raf kinase inhibitor, sorafenib, sorafenib analogs, and IDDBCP150446, among others) and closely related Anti-VEGF agents; BMS-387032 (Sunesis and Bristol-Myers Squibb) (also called SNS-032 and CAS Registry Number 345627-80-7, among others) and closely related Anti-VEGF agents; CEP-7055 (Cephalon and Sanofi-aventis) (also called CEP-11981 and SSR-106462, among others) and closely related Anti-VEGF agents; CHIR-258 (Chiron) (also called CAS Registry Number 405169-16-6, GFKI, and GFKI-258, among others) and closely related Anti-VEGF agents; CP-547632 (OSI Pharmaceuticals and Pfizer) (also called CAS Registry Number 252003-65-9, among others) and closely related Anti-VEGF agents such as, for instance, CP-564959; E-7080 (Eisai Co.) (also called CAS Registry Number 417716-92-8 and ER-203492-00, among others) and closely related Anti-VEGF agents; 786034 (GlaxoSmithKline) and closely related Anti-VEGF agents; GW-654652 (GlaxoSmithKline) and closely related indazolylpyrimidine Kdr inhibitors; IMC-1C11 (ImClone) (also called DC-101 and c-p1C11, among others) and closely related Anti-VEGF agents; KRN-951 (Kirin Brewery Co.) and other closely related quinoline-urea Anti-VEGF agents; PKC-412 (Novartis) (also called CAS Registry Number 120685-11-2, benzoylstaurosporine, CGP-41251, midostaurin, and STI-412, among others) and closely related Anti-VEGF agents; PTK-787 (Novartis and Schering) (also called CAS Registry Numbers 212141-54-3 and 212142-18-2, PTK/ZK, PTK-787/ZK-222584, ZK-22584, VEGF-TKI, VEGF-RKI, PTK-787A, DE-00268, CGP-79787, CGP-79787D, vatalanib, ZK-222584, among others) and closely related anilinophthalazine derivative Anti-VEGF agents; SU11248 (Sugen and Pfizer) (also called SU-11248, SU-011248, SU-11248J, Sutent®, and sunitinib malate, among others) and closely related Anti-VEGF agents; SU-5416 (Sugen and Pfizer/Pharmacia) (also called CAS Registry Number 194413-58-6, semaxanib, 204005-46-9, among others) and closely related Anti-VEGF agents; SU-6668 (Sugen and Taiho) (also called CAS Registry Number 252916-29-3, SU-006668, and TSU-68, among others) and closely related Anti-VEGF agents as described in, among others, WO-09948868, WO-09961422, and WO-00038519, particularly in parts pertaining to SU-6668 and closely related Anti-VEGF agents, their structures and properties, and methods for making and using them; VEGF Trap (Regeneron and Sanofi-aventis) (also called AVE-0005 and Systemic VEGF Trap, among others) and closely related Anti-VEGF agents as described in, among others, WO-2004110490, particularly in parts pertaining to VEGF Trap and closely related Anti-VEGF agents, their structures and properties, and methods for making and using them; Thalidomide (Celgene) (also called CAS Registry Number 50-35-1, Synovir, Thalidomide Pharmion, and Thalomid, among others) and closely related Anti-VEGF agents; XL-647 (Exelixis) (also called EXEL-7647, among others) and closely related Anti-VEGF agents; XL-999 (Exelixis) (also called EXEL-0999, among others) and closely related Anti-VEGF agents; XL-880 (Exelixis) (also called EXEL-2880, among others) and closely related Anti-VEGF agents; ZD-6474 (AstraZeneca) (also called CAS Registry Number 443913-73-3, Zactima, and AZD-6474, among others) and closely related anilinoquinazoline Anti-VEGF agents; and ZK-304709 (Schering) (also called CDK inhibitors (indirubin derivatives), ZK-CDK, MTGI, and multi-target tumor growth inhibitor, among others) and other closely related compounds including the indirubin derivative Anti-VEGF agents described in WO-00234717, WO-02074742, WO-02100401, WO-00244148, WO-02096888, WO-03029223, WO-02092079, and WO-02094814, particularly in parts pertinent to these and closely related Anti-VEGF agents, their structures and properties, and methods for making and using them.

Anti-VEGF agents may be delivered in a manner appropriate to the nature of the inhibitor, e.g. as a protein, small molecule, nucleic acid, etc., including without limitation appropriate vehicles and vectors as required.

Methods of Treatment

As summarized above, aspects of the instant disclosure include methods of treating a subject for treatment of proliferative vitreoretinopathy (PVR). The method for inhibiting or reducing the severity of proliferative vitreoretinopathy (PVR) in a subject comprises contacting retinal pigment epithelial cells in an eye of the subject with a composition comprising growth differentiation factor 15 (GDF-15) in a sufficient amount that inhibiting or reducing the severity of PVR.

Inhibiting or reducing the severity of PVR may result in an improvement visual acuity, reduction the risk of PVR reoccurrence once treatment has begun, increase the rate or likelihood of retinal reattachment following rhegmatogenous retinal detachment surgery, or improvement of the amelioration of any other symptoms associated with PVR.

The GF15 or a variant thereof is administered at a dosage, alone or in combination with other agents, that enhances neuron recovery while minimizing any side-effects. The effectiveness of recovery may be assessed, for example, by monitoring function of the neuron, e.g. maintenance or recovery of vision in PVR patients, such as at least about 5% recovery, at least about 10% recovery, at least about 20%, at least about 30%, at least about 40%, at least about 50%, at least about 75%, at least about 85%, at least about 95% or more, e.g. assessing by conventional measures of vision or retinal structure. It is contemplated that compositions will be obtained and used under the guidance of a physician for in vivo use. The dosage of the therapeutic formulation will vary widely, depending upon the nature of the disease, the frequency of administration, the manner of administration, the clearance of the agent from the host, and the like.

In some embodiments, the presently disclosed methods produce at least about a 10%, 15%, 20%, 25%, 30%, 35%, 40%, 45%, 50%, 55%, 60%, 65%, 70%, 75%, 80%, 85%, 90%, 95%, or even 100% decrease in loss of function, e.g. visual acuity, relative to function measured in absence of the GDF15 agent. Treatment may result in at least about a 10%, 15%, 20%, 25%, 30%, 35%, 40%, 45%, 50%, 55%, 60%, 65%, 70%, 75%, 80%, 85%, 90%, 95%, or even 100% decrease in symptoms of PVR, compared to a subject that is not treated with a GDF15 agent.

In some embodiments, treatment may result in reduced risk of PVR reoccurrence. For instances, risk of PVR reoccurrence may be reduced by at least 10%, 15%, 20%, 25%, 30%, 35%, 40%, 45%, 50%, 55%, 60%, 65%, 70%, 75%, 80%, 85%, 90%, 95%, or even reduced by 100% relative to the risk of PVR reoccurrence in a subject that is not treated with a GDF15 agent. In some embodiments, treatment may result in an increased rate of retinal reattachment in rhegmatogenous retinal detachment surgery. For instance, retinal reattachment rate may be increased by at least 10%, 15%, 20%, 25%, 30%, 35%, 40%, 45%, 50%, 55%, 60%, 65%, 70%, 75%, 80%, 85%, 90%, 95%, or even reduced by 100% relative to the rate of retinal reattachment in a subject that is not treated with a GDF15 agent.

GDF15 or a variant thereof may be administered at a concentration ranging from 0.1 μM to 10 mM, e.g., between 0.5 μM and 1 mM; between 1.0 μM and 500 μM; between 2.0 μM and 250 μM; at a dose of from about 0.1 ml to 1 ml/day, or scaled-up to an amount appropriate for human therapy. GDF15 may present in the compositions of the present invention at a concentration range of 0.1-10%, with preferred ranges between 1-5% and 2-2.5% (mg/ml). Exemplary liquid formulations for eye drops contain 2-2.5% (mg/ml) of the composition. Preferred formulations are in the form of a solid, a paste, an ointment, a gel, a liquid, an aerosol, a mist, a polymer, a film, an emulsion, or a suspension. The formulations are usually administered intravitreally or subconjunctivally.

The composition may be administered every 96 hours, every 72 hours, every 48 hours, every 24 hours, every 12 hours, every 6 hours, every 3 hours, or every 1 hour. The composition is administered for a duration of 1 day, 2 days, 3 days, 5 days, 7 days, 10 days, 14 days, 20 days, 30 days, 60 days, 90 days, 120 days, 180 days, or 365 days. For example, GDF15 is administered intravitreally or subconjunctively once per day for 7 days.

In one embodiment, the administration is intravitreal injection. Preferably, multiple intravitreal injections are administered to the subject over a period of at least 7 days, at least 14 days, at least 28 days. The multiple injections can be every day, every other day, every three days, every four days, every five days, every six days, or weekly for the duration of the treatment.

In another embodiment, the administration is subconjunctival. For subconjunctival administration, a single administration may be preferred, where the GDF15 is administered in a formulation suitable for sustained-release or slow-release of the active ingredient, such that it is disseminated to or throughout the retina and/or proximal ocular tissues over time, for example, over at least one week, two weeks, three weeks, one month, or two months. Suitable formulations for a single administration include, but are not limited to, membranes, gels, creams, wafers, sponges, or degradable pellets.

The composition may be administered at any time deemed necessary by a physician. For instance, the composition may be administered to an individual who is at risk for PVR but PVR has not yet developed such as an individual presenting the risk factors described above. The composition may also be administered to an individual once PVR has developed. The composition may also be administered to an individual following rhegmatogenous retinal detachment surgery.

Also within the present disclosure is a pharmaceutical composition comprising GDF-15 or a variant thereof, and a pharmaceutically acceptable carrier and/or ophthalmic excipient. The pharmaceutical composition is for use for inhibiting or reducing the severity of proliferative vitreoretinopathy (PVR). Exemplary pharmaceutically acceptable carriers include a compound selected from the group consisting of a physiological acceptable salt, poloxamer analogs with carbopol, carbopol/hydroxypropyl methyl cellulose (HPMC), carbopol-methyl cellulose, carboxymethylcellulose (CMC), hyaluronic acid, cyclodextrin, and petroleum.

All compounds of the invention are purified and/or isolated. Specifically, as used herein, an “isolated” or “purified” polypeptide or protein is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. Purified also defines a degree of sterility Pharmaceutical Compositions For administration to a subject such as a human or other mammal (e.g., companion, zoological or livestock animal), GDF15 or a variant thereof is desirably formulated into a pharmaceutical composition containing the active agent in admixture with one or more pharmaceutically acceptable diluents, excipients, or carriers. Examples of such suitable excipients for can be found in U.S. Publication 2009/0298785 (incorporated by reference herein in its entirety), the Handbook of Pharmaceutical Excipients, 2nd Edition (1994), Wade and Weller, eds. Acceptable carriers or diluents for therapeutic use are well-known in the pharmaceutical art, and are described, for example, in Remington: The Science and Practice of Pharmacy, 20th Edition (2000) Alfonso R. Gennaro, ed., Lippincott Williams & Wilkins: Philadelphia, Pa.

The choice of pharmaceutical earlier, excipient or diluent can be selected with regard to the intended route of administration and standard pharmaceutical practice. The pharmaceutical composition can contain as, or in addition to, the carrier, excipient or diluent any suitable binder(s), lubricant(s), suspending agent(s), coating agent(s), solubilizing agent(s), etc.

A person of ordinary skill in the art can easily determine an appropriate dosage to administer to a subject without undue experimentation. Typically, a physician will determine the actual dosage that will be most suitable for an individual subject based upon a variety of factors including the activity of the specific compound employed, the metabolic stability and length of action of the compound, the age, body weight, general health, diet, mode and time of administration, rate of excretion, drug combination, the severity of the particular condition, and the individual undergoing therapy. To determine a suitable dose, the physician or veterinarian could start doses levels lower than that required in order to achieve the desired therapeutic effect and gradually increase the dosage until the desired effect is achieved. This is considered to be within the skill of the artisan and one can review the existing literature on a specific agent to determine optimal dosing.

In some embodiments, the composition is administered in the form of a liquid (e.g., drop or spray) or gel suspension. Alternatively, the composition is applied to the eye via liposomes or infused into the tear film via a pump-catheter system. Further embodiments embrace a continuous or selective-release device, for example, membranes such as, but not limited to, those employed in the OCUSERT System (Alza Corp., Palo Alto. Calif.) in an alternative embodiment, the GD15 is contained within, carried by, or attached to a contact lens, which is placed on the eye. Still other embodiments embrace the use of the composition within a swab or sponge, which is applied to the ocular surface.

In some cases, the composition further comprises a pharmaceutically acceptable carrier, e.g., a pharmaceutically acceptable salt. Suitable ocular formulation excipients include FDA approved ophthalmic excipients, e.g., emulsions, solutions, solution drops, suspensions, and suspension drops. Other suitable classifications include gels, ointments, and inserts/implants.

Exemplary excipients for use in optimizing ocular formulations include alcohol, castor oil, glycerin, polyoxyl 35 castor oil, Tyloxapol, polyethylene glycol 8000 (PEG-8000), ethanol, glycerin, cremaphor, propylene glycol (pG), polypropylene glycol (ppG), and polysorbate 80. In some cases, citrate buffer and sodium hydroxide are included to adjust pH. Preferably, the formulation for ocular delivery of nutlin-3a comprises 5% cremaphor, 10% pG, 15% pPG, and 70% phosphate buffered saline (PBS).

In certain embodiments, the presently disclosed subject matter also includes combination therapies. Depending on the particular disease, disorder, or condition to be treated or prevented, additional therapeutic agents, which are normally administered to treat or prevent that condition, may be administered in combination with the compounds of this disclosure. These additional agents may be administered separately, as part of a multiple dosage regimen. Alternatively, these agents may be part of a single dosage form, mixed together with the GDF15 polypeptide.

By "in combination with" is meant the administration of GF15 or a variant thereof, or other compounds disclosed herein, with one or more therapeutic agents either simultaneously, sequentially, or a combination thereof. Therefore, a cell or a subject administered a combination of GF15 or a variant thereof, can receive one or more therapeutic agents at the same time (i.e., simultaneously) or at different times (i.e., sequentially, in either order, on the same day or on different days), so long as the effect of the combination of both agents is achieved in the cell or the subject. When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where the GF15 or a variant thereof and one or more therapeutic agents are administered simultaneously, they can be administered to the cell or administered to the subject as separate pharmaceutical compositions, or they can contact the cell as a single composition or be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times. In such combination therapies, the therapeutic effect of the first administered compound is not diminished by the sequential, simultaneous, or separate administration of the subsequent compound(s).

Also provided are a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In some embodiments, the kits comprise one or more containers, including, but not limited to a vial, tube, ampule, bottle and the like, for containing the compound. The one or more containers also can be carried within a suitable carrier, such as a box, carton, tube or the like. Such containers can be made of plastic, glass, laminated paper, metal foil, or other materials suitable for holding medicaments.

In some embodiments, the container can hold a composition that is by itself or when combined with another composition effective for treating or preventing the condition and may have a sterile access port (for example the container may be an intravenous solution bag or a vial having a stopper pierceable by a hypodermic injection needle). Alternatively, or additionally, the article of manufacture may further include a second (or third) container including a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The presently disclosed kits or pharmaceutical systems also can include associated instructions for using the compounds for treating or preventing a neurodegenerative disease, disorder, or condition, e.g. optic neuritis, including glaucoma. In some embodiments, the instructions include one or more of the following: a description of the active compound; a dosage schedule and administration; precautions; warnings; indications; counter-indications; overdosage information; adverse reactions; animal pharmacology; clinical studies; and references. The instructions can be printed directly on a container (when present), as a label applied to the container, as a separate sheet, pamphlet, card, or folder supplied in or with the container.

EXPERIMENTAL

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Example 1

As shown in FIG. 1, Smad2 inhibition (A) or simultaneous culture with GDF-15 (B) blocks GDF-11-induced upregulation of EMT marker Fibronectin in ESC-NPCs. (A) ESC-derived NPCs were pre-treated with DMSO or Smad2 inhibitor SB431542 (10 μM) for 1 h and then co-treated with PBS or GDF-11 (50 ng/ml) for another 7 days before harvest. (B) SC-derived NPCs were pre-treated with PBS or GDF-15 (50 ng/ml) for 1 h and then co-treated with PBS or GDF-11 (16.7 ng/ml) for another 7 days before harvest. GDF-15 was added daily while SB431542 and GDF-11 was only added one time in the beginning. Nucleus (DPAI) and EMT (Fibronectin) marker were then detected by immunofluorescence.

Figure 2:
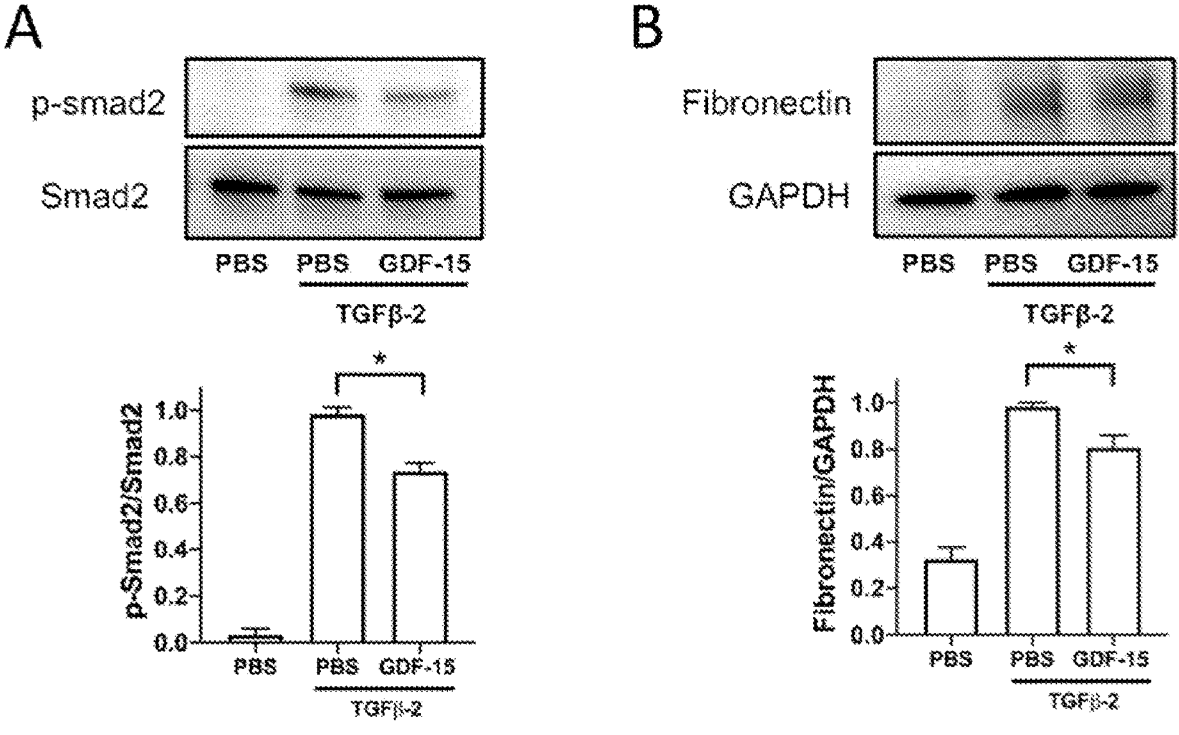
FIG. 2: Simultaneous culture with GDF-15 reduces TGFβ-2-induced upregulation of phosph-Smad2 (A) and EMT marker Fibronectin (B) in ARPE-19 cells. (N=3, *$P<0.05$).

As shown in FIG. 2, simultaneous culture with GDF-15 reduces TGFβ-2-induced upregulation of phosph-Smad2 (A) and EMT marker Fibronectin (B) in ARPE-19 cells. (N=3, $*P<0.05$). Human adult retinal pigment epithelial cells (ARPE-19) were pre-treated with PBS or GDF-15 (50 ng/ml) for 1 h and then co-treated with PBS or TGFβ-2 (1 ng/ml) for another hour (A) or 2 days (B) before harvest. For Fibronection detection, GDF-15 was added daily while TGFβ-2 was only added one time in the beginning. GAPDH (loading control), p-Smad2 and Fibronectin proteins were then detected by Western blot.

What is claimed is:

1. A method for inhibiting or reducing the severity of proliferative vitreoretinopathy (PVR) in a human subject, the method comprising:

contacting retinal pigment epithelial cells in an eye of the human subject with a composition comprising human growth differentiation factor 15 (GDF-15) in an amount sufficient to inhibit or reduce the severity of PVR.

2. The method of claim 1, wherein the composition is administered intravitreally or subconjunctivally.

3. The method of claim 1, wherein the subject suffering from PVR has undergone rhegmatogenous retinal detachment surgery.

4. The method of claim 1, wherein the amount of GDF-15 sufficient to inhibit or reduce the severity of PVR reduces epithelial-mesenchymal transformation of retinal epithelial cells.

5. The method of claim 1, wherein said composition prevents retinal detachment in said subject.

6. The method of claim 1, wherein said composition reduces the formation of epiretinal membranes in said subject.

7. The method of claim 1, wherein said composition inhibits the contraction of retinal pigment epithelial (RPE) cells in said subject.

8. The method of claim 1, wherein said composition is administered every 48 hours, every 24 hours, every 12 hours, or every 6 hours.

9. The method of claim 1, wherein said composition is administered for 1 day, 3 days, 7 days, 14 days, 30 days, 60 days or more.

10. The method of claim 1, wherein said composition further comprises a pharmaceutically acceptable carrier.

11. The method of claim 1, wherein the composition is administered prior to the development of PVR.

12. The method of claim 1, wherein the composition is administered after the development of PVR.

13. The method of claim 1, wherein the composition is administered following rhegmatogenous retinal detachment surgery.

14. The method of claim 1, wherein the amount of GDF-15 sufficient to inhibit or reduce the severity of PVR improves visual acuity.

15. The method of claim 1, wherein the amount of GDF-15 sufficient to inhibit or reduce the severity of PVR reduces the risk of PVR reoccurrence.

16. The method of claim 1, wherein the amount of GDF-15 sufficient to inhibit or reduce the severity of PVR improves the likelihood of retinal reattachment following rhegmatogenous retinal detachment surgery.

* * * * *

SEQUENCE LISTING

```
<160> NUMBER OF SEQ ID NOS: 1

<210> SEQ ID NO 1
<211> LENGTH: 308
<212> TYPE: PRT
<213> ORGANISM: Homo sapiens

<400> SEQUENCE: 1

Met Pro Gly Gln Glu Leu Arg Thr Val Asn Gly Ser Gln Met Leu Leu
1               5                   10                  15

Val Leu Leu Val Leu Ser Trp Leu Pro His Gly Gly Ala Leu Ser Leu
            20                  25                  30

Ala Glu Ala Ser Arg Ala Ser Phe Pro Gly Pro Ser Glu Leu His Ser
        35                  40                  45

Glu Asp Ser Arg Phe Arg Glu Leu Arg Lys Arg Tyr Glu Asp Leu Leu
    50                  55                  60

Thr Arg Leu Arg Ala Asn Gln Ser Trp Glu Asp Ser Asn Thr Asp Leu
65                  70                  75                  80

Val Pro Ala Pro Ala Val Arg Ile Leu Thr Pro Glu Val Arg Leu Gly
                85                  90                  95

Ser Gly Gly His Leu His Leu Arg Ile Ser Arg Ala Ala Leu Pro Glu
            100                 105                 110

Gly Leu Pro Glu Ala Ser Arg Leu His Arg Ala Leu Phe Arg Leu Ser
        115                 120                 125
```

-continued

```
Pro Thr Ala Ser Arg Ser Trp Asp Val Thr Arg Pro Leu Arg Arg Gln
    130                 135                 140

Leu Ser Leu Ala Arg Pro Gln Ala Pro Ala Leu His Leu Arg Leu Ser
145                 150                 155                 160

Pro Pro Pro Ser Gln Ser Asp Gln Leu Leu Ala Glu Ser Ser Ser Ala
                165                 170                 175

Arg Pro Gln Leu Glu Leu His Leu Arg Pro Gln Ala Ala Arg Gly Arg
            180                 185                 190

Arg Arg Ala Arg Ala Arg Asn Gly Asp His Cys Pro Leu Gly Pro Gly
        195                 200                 205

Arg Cys Cys Arg Leu His Thr Val Arg Ala Ser Leu Glu Asp Leu Gly
    210                 215                 220

Trp Ala Asp Trp Val Leu Ser Pro Arg Glu Val Gln Val Thr Met Cys
225                 230                 235                 240

Ile Gly Ala Cys Pro Ser Gln Phe Arg Ala Ala Asn Met His Ala Gln
                245                 250                 255

Ile Lys Thr Ser Leu His Arg Leu Lys Pro Asp Thr Val Pro Ala Pro
            260                 265                 270

Cys Cys Val Pro Ala Ser Tyr Asn Pro Met Val Leu Ile Gln Lys Thr
        275                 280                 285

Asp Thr Gly Val Ser Leu Gln Thr Tyr Asp Asp Leu Leu Ala Lys Asp
    290                 295                 300

Cys His Cys Ile
305
```